US00PP08714P

United States Patent [19]

Cobia

[11] Patent Number: Plant 8,714

[45] Date of Patent: May 3, 1994

[54] PLANT OF THE CACTACEAE PLANT FAMILY NAMED 'ASHLEY'

[76] Inventor: Barnell L. Cobia, P.O. Box 771369, Winter Garden, Fla. 34777-1369

[21] Appl. No.: 35,325

[22] Filed: Mar. 22, 1993

[51] Int. Cl.[5] ..... A01H 5/00

[52] U.S. Cl. ..... Plt./88.5

[58] Field of Search ..... Plt. 88.5

*Primary Examiner*—James R. Feyrer

*Attorney, Agent, or Firm*—Roger L. Martin

[57] ABSTRACT

A new and distinct plant variety of the Cactaceae family is of the type known commercially as a 'Spring Cactus' and has growth characteristics which are similar to those of the 'Scarlet O'Hara' variety, but which are nevertheless modified by a combination of characteristics that include among others: flowers that have shorter and narrower tube laminating tepals, and different dominating hues of color in the tube laminating and tube forming tepals.

2 Drawing Sheets

BACKGROUND OF THE INVENTION

The invention relates to a new and distinct plant variety of the Cactaceae family which has been named *Rhipsalidopsis gaertneri* 'Ashley' by the inventor.

Certain plant varieties of the Cactaceae family are well known in the foliage plant market and among these are those which are commonly referred to as the Spring or Easter cactus varieties because they tend to bloom in the Spring of the year.

The Spring cactus varieties on the market have blooms which vary in color from one variety to the next and are generally dominated by a red or closely related hue. One such cultivar in the marketplace at the time of application is 'Scarlet O'Hara' having a red flower.

SUMMARY OF THE INVENTION

A general objective has been to develop a new plant variety which is distinguishable from the 'Scarlet O'-Hara' variety and which is capable of being marketed competitively therewith.

The objective has been fully realized in the development of the new plant variety hereinafter described in detail. The new plant variety was developed in a nursery located at Winter Garden, Fla., as an offspring secured by the self pollination of an unnamed research variety that is a descendent of the 'Scarlet O'Hara' variety. The seeds taken from the fertilized seed pod were cultivated at the mentioned nursery location and after prolonged observation of the seedlings, the seedling of the new plant variety was selected and asexually reproduced by the invertor at the Winter Garden nursery by propagation of stem cuttings taken from the original seedling plant.

Through successive propagation, it has been ascertained that specimens of the new plant variety are distinguishable from specimens of the 'Scarlet O'Hara' variety and other related varieties known to the inventor by a growth habit which is evident in plant specimens of the new plant variety that have been propagated and grown under nursery conditions utilized in the growing of topical plants in Winter Garden, Fla., as combining the following characteristics:

1. Flowers which, in comparison to the 'Scarlet O'-Hara' variety, have (a) a tube laminating tepal series with generally shorter length dimensions and generally smaller width dimensions, (b) a tube forming tepal series with generally shorter length dimensions and generally smaller width dimensions, (c) tube laminating and tube forming tepal series that are generally dominated by hues of orange, reddish orange, red and pink hues whereas the tepals of the 'Scarlet O'Hara' variety are generally dominated by hues of red, purplish red, and pink.

BRIEF DESCRIPTION OF THE DRAWINGS

The accompanying drawings serve by color photographic means to illustrate the new plant variety and wherein one sheet shows a ten (10) month old specimen which was grown from the propagation of a single phylloclade in a conventional 3½" plastic pot (trade designation) found in the marketplace.

A second sheet shows an enlargement of a fully open bloom taken from the specimen shown in the first mentioned sheet compared to a second bloom that has been taken from the same specimen and sectioned generally longitudinally through the perianth tube and ovary to expose the style and stamen arrangements.

DETAILED PLANT DESCRIPTION

The following is a detailed description of the new plant variety with colors and hues, unless otherwise clearly indicated by the text as, for example, through the absence of color notations, being named in accord with the ISCC-NBS Method of Designating colors (U.S. Dept. of Commerce, National Bureau of Standards, Circular 553), the named colors being interpreted from color specimens of the Munsell Book of Color. The description is further based on observations of well fertilized plants of about ten (10) months of age from initial propagation which were grown under 50%-75% shaded greenhouse nursery conditions in the Winter Garden, Fla. area and wherein temperatures range from 60°-85° F. during the winter months, from 75°-95° F. during the summer months, and are ambient during the intervening periods.

I. Name: *Rhipsalidopsis gaertneri* 'Ashley'.

II. Parentage: The new variety is the result of the self pollination of an unnamed research variety having a generally red bloom and designated as EH1918. The research variety designated EH1918 was a result of self pollination of the variety known as 'Scarlet O'-Hara'.

III. Classification:

A. *Botanic* (*Tropica, Roehrs Company, New Jersey* 1978).—(1) Family: Cactaceae. (2) Tribe: Cereeae. (3) Sub-Tribe: Rhipsalidanae. (4) Genus: Rhipsalidopsis. (5) Species: *gaertneri.*

B. *Commercial.*—Spring or Easter cactus.

IV. Form: Epiphytic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and lateral wings having crenate margins.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — extends longitudinally of phylloclade and continuously through joints and with a laterally tapering cortex at the wing insertions. Pith surrounding vascular bundles that branch and provide lateral extensions of the vascular system to the marginal rounded teeth. (b) Texture — Smooth, waxy epidermis with was in small embedded scales and becoming woody in basal stem areas with specimen aging. (c) Size (at maturity) — 1. Length: Range: Usually 37–65 mm. Mean: 53.2 mm. Std. Dev.: 8.30 mm. 2. Thickness: Range: Usually 3.0–5.5 mm. Mean: 4.5 mm. Std. Dev.: 0.64 mm. (d) Color (at maturity) — Usually dominated by a yellow green hue. Commonly moderate yellow green (7.5 GY 5/6) and/or strong yellow green (7.5 GY 6/8). (3) Wings: (a) Crenate and generally flattened from midrib cortex to tooth insertions and with slight thinning taper towards margins. (b) Margins — Crenate. (c) Texture — Succulent to leathery with smooth, waxy epidermis where the wax is arranged in small embedded scales of higher density than in midrib area, and becoming corky in the basal stem area, and becoming corky in the basal stem areas with specimen aging. (d) Size (at maturity) — 1. Width: Range: Usually 9–16 mm. Mean: 12.7 mm. Std. Dev.: 2.30 mm. 2. Thickness: Range: Usually 1.5–3.0 mm. Mean: 2.3 mm. Std. Dev.: 0.47 mm. (e) Color (at maturity) — Usually dominated by a yellow green and/or olive green hue. Commonly moderate yellow green (7.5 GY 5/6) and/or moderate olive green (7.5 GY 4/6). (4) Teeth: (a) Shape — 1. General: Generally flattened and tapered along the margins and from the wing insertions to the margin, and are crenate in shape. (b) Orientation — Generally project distally of phylloclade in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Range: Usually 1.0–1.5 mm. Mean: 1.2 mm. Std. Dev.: 0.25 mm. (f) Number — Usually 6–8 per phylloclade. (g) Color (at maturity) — Usually dominated by an olive green hue. Commonly moderate olive green (7.5 GY 4/6) (7.5 GY 4/4) (7.5 GY 3/4). (b 5) Areoles: (a) Terminal areole — Large, elongated, oval shaped with several acicular bristles, and several buds that may mature into either new phylloclades or flowers. The opposite ends of the areoles are located adjacent to subsidiary areoles which are in turn located at the axils of the teeth at the distal end of the phylloclade. (b) Axillary areoles — acicular bristles without glochidia but having copious, short, brownish, multicellular, wooly hairs, In areoles located below the teeth at the distal end of the phylloclade, there is usually only one areole which is frequently latent.

VI. Buds: Unarmored, ovoid.

VII. Flowers:

A. *General.*—Sessile, zygomorphic, usually solitary, terminal, perfect and epigynous with double hypanthium and whorled tepals (undifferentiated sepals and petals) having a spiral emergence as a perianth that is nearly rotate in structure and having a short tube, provided with a sepaloid series of free tepals, a tube laminating series of tepals, and a tube forming series of united tepals.

B. Sepaloid series.—(1) General: Free tepals inserted on top of ovary. (2) Shape: Deltoid in outer members of whorl and grading inwardly to lanceolate and providing greater length dimensions and broader apices. All members have a pointed tip and entire margins. (3) Texture: Succulent and glabrous outer whorl members and grading inwardly in whorl to silken blades with fleshy basal areas. (4) Number: Usually 4–7. (5) Size (at full bloom): (a) Length (base-tip dimensions) Range: Usually less than 18 mm. Mean: 8.9 mm. Std. Dev.: 4.90 mm. (b) Width (maximum) Range: Usually less than 5 mm. Mean: 3.7 mm. Std. Dev.: 0.58 mm. (6) Color (at full bloom): Varies from the outer members to the inner members with the smallest outer whorl tepals usually having a continuous field that is color is dominated by a red hue. Marginal and center field areas of the inner whorl members are generally dominated by a red hue and merges proximally with a red and/or pink hue in the basal area. Commonly vivid red (5 R 4/14), and/or strong red (5 R 5/12) in the marginal and centerfield areas and merging proximally with strong red (5 R 5/12) and/or deep pink (5 R 6/10) in the basal areas of the inner whorl members. Commonly strong red (5 R 5/12), vivid red (5 R 4/14), and/or dark red (5 R 3/6) in the outer whorl members. (7) Orientation: Generally erect at full bloom.

C. *Tube laminating series.*—(1) General: Tepals inserted on ovary and basally united below the throat as outer lamination on the perianth tube and with progressively greater amount of basal fusion inwardly in the whorl. (2) Shape: Zygomorphic and grading inwardly in the whorl with progressively greater length dimensions with a blade area that is generally lanceolate and having acute to acuminate tips and entire margins. (3) Texture: Glabrous, silken blades with slightly fleshy basal areas. (4) Number: Usually 8–12. (5) Size (at full bloom) — (a) Length (base-tip dimension) Range: Usually 18–53 mm. Mean: 37.5 mm. Std. Dev.: 10.61 mm. (b) Width (maximum) — Range: Usually 4–8 mm. Mean: 6.3 mm. Std. Dev.: 0.83 mm. (6) Color (at full bloom): (a) General — Tepals with a basal area that is usually dominated by a pinkish white and/or yellowish hue immediately above the insertion that merges distally into a center blade area that is dominated by an orange, and/or reddish orange hue. Center blade area then continues to merge distally into a marginal blade area that is color is dominated by a red and/or pink hue. (b) Basal area — Commonly pinkish white (2.5 YR 9/1) and/or pale yellowish pink (2.5 YR 9/2) at insertion. (c) Blade area — Commonly moderate orange (2.5 YR 7/10) (2.5 YR 7/8), strong orange (2.5 YR 7/10), strong reddish orange (7.5 R 5/12) and/or moderate reddish orange (7.5 R 6/10) in the center field areas and merging distally with the marginal blade area that is commonly vivid red (5 R 4/14), strong red (5 R 5/12) and/or deep pink (5 R 6/10). (7) Orientation: Generally ranging from being erect to being perpendicular to the perianth tube.

D. *Tube forming series.*—(1) General: Tepals basally united to form a short hollow perianth tube that is inserted on ovary. (2) Shape: (a) Perianth tube — Short and circular in cross section. (b) Blades — Nearly zygomorphic and generally lanceolate with acuminate to acute tips and entire margins. (3) Texture: (a) Perianth tube — Thick, succulent and slightly ribbed. (b) Blades — Translucent and silken. (4) Number: Usually 8–9. (5) Size (at full bloom): (a) Perianth tube — 1. Length (measured from top of ovary) Range: Usually 4–6 mm. Mean: 5.0 mm. Std. Dev.: 0.71 mm. 2. Diameter: Range: Usually 4–6 mm. Mean: 4.9 mm. Std. Dev.: 0.55 mm. (b) Blades — 1. Length (base-tip): Range: Usually 40–52 mm. Mean: 46.9 mm. Std. Dev.: 2.44 mm. 2. Width (maximum): Range: Usually 5–8 mm. Mean: 6.7 mm. Std. Dev.: 0.76 mm. (6) Color (at full bloom): (a) Perianth tube — A basic field that is generally dominated by a pinkish white and/or yellowish pink hue. Commonly pinkish white (5 YR 9/1) and/or pale yellowish pink (5 YR 9/2). (b) Blades — A center blade area that is generally dominated by an orange and/or reddish orange hue, and merging distally with a marginal blade area that is generally dominated by a reddish orange and/or red hue. Generally dominated by a pinkish white and/or yellowish pink hue in the basal area at insertion. Commonly moderate yellowish orange (7.5 R 5/10) (7.5 R 6/10), moderate orange (2.5 YR 7/10), and/or strong orange (2.5 YR 7/10) in the center field areas and becoming strong red (5 R 5/12) and/or strong reddish orange (7.5 R 5/12) in the marginal blade areas. Commonly pinkish white (5 YR 9/1) and/or pale yellowish pink (5 YR 9/2) at insertion. (7) Orientation: Obtuse to recurve.

E. *Androecium (stamens).*—(1) General: Numerous exerted and diadelphous stamens having filaments basally fused to the perianth tube, thin annulus around the style and which is provided with thin, deflexed, irregular, toothed margin or ruffle at the throat of the annulus. (2) Stamen number: Usually 125–167. (3) Filaments: (a) General — Translucent with anther connective. (b) Shape — Long, slender, terete. (c) Texture — Glabrous and capillaceous. (d) Color — Generally dominated by a reddish purple hue at the distal end and merging with an orange hue intermediate the opposing ends and becoming a pinkish white and/or yellowish pink hue in the basal area. Commonly strong reddish purple (2.5 RP 5/10) (2.5 RP 4/10) in the distal end and becoming strong orange (2.5 YR 7/10) and/or moderate orange (2.5 YR 7/8) in the intermediate area, and pinkish white (5 YR 9/1) and/or pale yellowish pink (5 YR 9/2) in the basal areas. (e) Size (at full bloom): 1. Length: Range: Usually 6–22 mm. Mean: 14.1 mm. Std. Dev.: 5.76 mm. 2. Diameter: Usually 0.20–0.25 intermediate opposite ends. (4) Anthers: (a) General — Adnate with four longitudinally dehiscent pollen sacs and connective inserted at end. (b) Shape —Elongated. (c) Texture — Waxy. (d) Color (before dehiscence) — Dominated by a greenish yellow hue. Commonly brilliant greenish yellow (7.5 YR 9/10) and/or vivid greenish yellow (7.5 R 8.5/12).

F. *Gynoecium (pistil).*—(1) General: Exerted with compound, pariental placentation and united style surrounded by annular diffuse yellowish nectary at its insertion. (2) Style: (a) General — Hollow, stout and inserted at ovary. (b) Shape — Elongated and terete. (c) Texture — Fleshy and smooth. (d) Color — Usually dominated by a reddish orange hue. Commonly moderate reddish orange (7.5 R 6/10) and/or strong reddish orange (7.5 R 5/12). (e) Size (at full bloom) — 1. Length: Range: Usually 10–18 mm. Mean: 14.7 mm. Std. Dev.: 3.04 mm. 2. Diameter: Usually 0.75–1.0 mm. (3) Stigma: (a) General — exerted and erect to recurve with usually 6–8 marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Usually dominated by a pinkish white hue. Commonly pinkish white (2.5 R 9/1) (5 R 9/1). (e) Size — 1. Length: Range: Usually 4–6 mm. Mean: 5.1 mm. Std. Dev.: 0.78 mm. (4) Ovary: (a) General — Inferior with thin epidermis and usually 5–7 carpules with numerous ovules. (b) Shape — Terete to ovoid and generally broadening from insertion to floral end. Generally having five (5) prominent longitudinal ribs, single concavity, and having an inserted style. (c) Texture — Succulent with glabrous thin outer epidermis. (d) Color — A basic field with color usually dominated by a yellow green and/or olive green hue, with longitudinal ribs that are usually dominated by a red hue. Basic field commonly moderate olive green (5 GY 4/4), and/or moderate yellow green (5 GY 5/4) (5 GY 5/6). Longitudinal ribs commonly vivid red (5 R 4/14), strong red (5 R 4/14), and/or dark red (5 R 3/6). (e) Size — 1. Length: Range: Usually 9–11 mm. Mean: 10.0 mm. Std. Dev.: 0.71 mm. 2. Major axis: Range: Usually 8–10 mm. Mean: 9.0 mm. Std. Dev.: 0.63 mm. 3. Minor axis: Range: Usually 7–9 mm. Mean: 8.0 mm. Std. Dev.: 0.63 mm.

VIII. Growth habit: Erect.

GENERAL DESCRIPTION OF A PLANT SPECIMEN

Age of plant: 10 months from initial propagation of single phylloclade, having been pruned to the 2 tier level at approximately 5 months of age.

Branches from propagated phylloclade: 8.

Total number of new phylloclades grown: 19.

General:

| Branch Number | No. of Phylloclades | Maximum Length | No. of Tips |
|---|---|---|---|
| 1 | 2 | 50 mm. | 1 |
| 2 | 3 | 57 mm. | 2 |
| 3 | 2 | 48 mm. | 1 |
| 4 | 2 | 60 mm. | 1 |
| 5 | 3 | 58 mm. | 2 |
| 6 | 2 | 49 mm. | 1 |
| 7 | 2 | 58 mm. | 1 |
| 8 | 3 | 62 mm. | 2 |

Midribs:

| Branch Number | Average Midrib Length | Average Midrib Thickness |
|---|---|---|
| 1 | 57.7 mm. | 4.8 mm. |
| 2 | 53.0 mm. | 4.7 mm. |
| 3 | 58.5 mm. | 4.8 mm. |
| 4 | 56.0 mm. | 4.8 mm. |
| 5 | 60.7 mm. | 4.5 mm. |
| 6 | 54.0 mm. | 3.8 mm. |
| 7 | 43.5 mm. | 3.8 mm. |
| 8 | 46.0 mm. | 4.7 mm. |

Wings:

| Branch Number | Average Wing Thickness | Average Wing Width (maximum) |
|---|---|---|
| 1 | 2.0 mm. | 12.5 mm. |
| 2 | 2.5 mm. | 12.3 mm. |
| 3 | 2.5 mm. | 14.0 mm. |
| 4 | 2.8 mm. | 12.5 mm. |
| 5 | 2.7 mm. | 14.0 mm. |
| 6 | 2.0 mm. | 13.5 mm. |
| 7 | 1.8 mm. | 11.5 mm. |
| 8 | 1.8 mm. | 11.3 mm. |

Phylloclade color: Moderate olive green (7.5 GY 4/6) (7.5 GY 4/4) (7.5 GY 3/4), moderate yellow green (7.5 GY 5/6), strong yellow green (7.5 GY 6/8).

GENERAL DESCRIPTION OF A FLOWER

The following is a general description of a flower of the new plant variety and which was in full bloom in April on a 10 month old plant specimen grown under shaded greenhouse conditions in Winter Garden, Fla.

Number of buds and blooms on plant specimen: 32.

Bloom life: 8 days.

Sepaloid series of tepals:

*Number.*—6.

*Tepal size (at full bloom).*—Maximum base-tip dimension: 16 mm. Minimum base-tip dimension: 4 mm. Maximum width dimension: 4.5 mm. Minimum width dimension: 3 mm.

*Color (at full bloom).*—Strong red (5 R 5/12), vivid red (5 R 4/14) and dark red (5 R 3/6) in a continuous field of outer whorl members. Vivid red (5 R 4/14), and strong red (5 R 5/12) in marginal and center field areas and strong red (5 R 5/12) and deep pink (5 R 6/10) in the basal areas of inner whorl members.

Tube laminating series of tepals:

*Number.*—10.

*Size (at full bloom).*—Maximum base-tip dimension: 51 mm. Minimum base-tip dimension: 20 mm. Maximum blade width: 8 mm. Minimum blade width: 4 mm.

*Color (at full bloom).*—Moderate orange (2.5 YR 7/10) (2.5 YR 7/8), strong orange (2.5 YR 7/10), strong reddish orange (7.5 R 5/12) and moderate reddish orange (7.5 R 6/10) in centerfield areas; vivid red (5 R 4/14), strong red (5 R 5/12), and deep pink (5 R 6/10) in marginal blade area, and pale yellowish pink (2.5 YR 9/2) in the basal areas of the blade.

Tube forming series of tepals:

*Number.*—9.

*Size (at full bloom).*—Perianth tube: Length: 6 mm. Diameter: 4 mm. Blades: Maximum length (base-tip): 51 mm. Minimum length (base-tip): 46 mm. Maximum blade width: 8 mm. Minimum blade width: 7 mm.

*Color (at full bloom).*—Perianth tube: Pinkish white (5 YR 9/1) and pale yellowish pink (5 YR 9/2). Blades: Moderate yellowish orange (7.5 R 5/10), moderate orange (2.5 YR 7/10), and strong orange (2.5 YR 7/10) in the center field areas and becoming strong red (5 R 5/12) and strong reddish orange (7.5 R 5/12) in marginal blade areas. Pale yellowish pink (5 YR 9/2) at insertion.

Androecium:

*Stamen number.*—142.

*Filaments.*—Color: Strong reddish purple (2.5 RP 5/10) (2.5 RP 4/10) in the distal end, becoming strong orange (2.5 YR 7/10) and moderate orange (2.5 YR 7/8) in the intermediate area, and pinkish white (5 YR 9/1) and pale yellowish pink (5 YR 9/2) in the basal area.

*Size (at full bloom).*—Length: 15 mm. Diameter: About 0.20 mm intermediate the opposite ends.

*Anthers.*—Color (before dehiscing): Brilliant greenish yellow (7.5 Y 9/10).

Gynoecium (pistil):

*Style.*—Color: Moderate reddish orange (7.5 R 6/10) and strong reddish orange (7.5 R 5/12). Size (at full bloom): Length—16 mm. Diameter—About 1.0 mm. intermediate the opposite ends.

*Stigma.*—Color: Pinkish white (2.5 R 9/1) (5 R 9/1). Size: 5 mm. (avg.) lobe length.

*Ovary.*—Color: Basic field of moderate olive green (5 GY 4/4) and moderate yellow green (5 GY 5/4) (5 GY 5/6) with longitudinal ribs of dark red (5 R 3/6) and strong red (5 R 4/14). Size (at full bloom): Length (insertion to concavity base) — 10 mm. Major axis — 9 mm. at distal end of concavity. Minor axis — 8 mm. at distal end of concavity.

We claim:

1. A new and distinct plant variety of the Cactaceae family as shown and described and which is mainly distinguished from its antecedents and known related varieties by growth characteristics that are similar to those of the 'Scarlet O'Hara' variety but as modified by the combination of the following characteristics:

1. Flowers which, in comparison to the 'Scarlet O'Hara' variety, have (a) a tube laminating tepal series with generally shorter length dimensions and generally smaller width dimensions, (b) a tube forming tepal series with generally smaller width dimensions, (c) tube laminating and tube forming tepal series that are generally dominated by hues of orange, reddish orange, red and pink, whereas the tepals of the 'Scarlet O'Hara' variety are generally dominated by hues of red, purplish red, and pink.

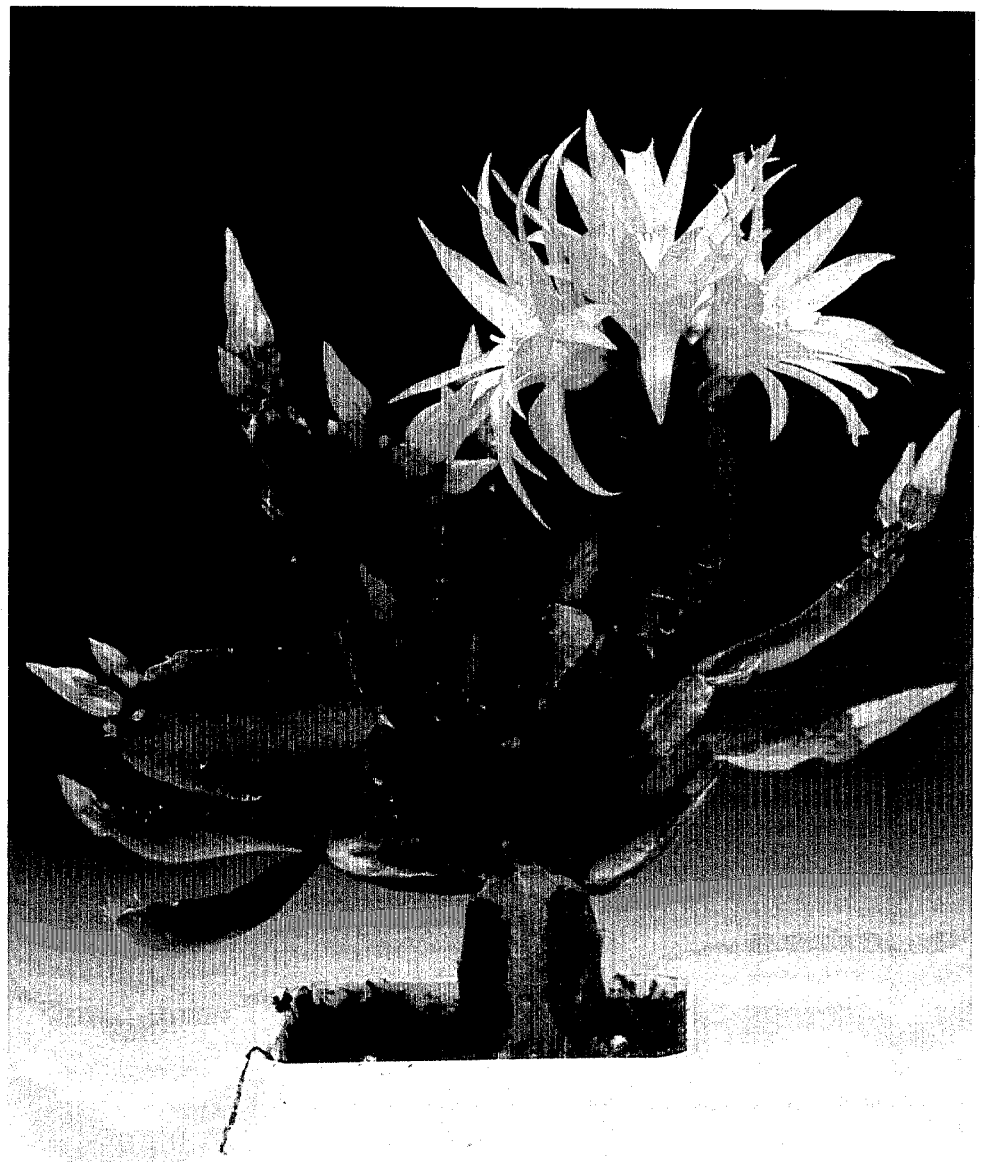

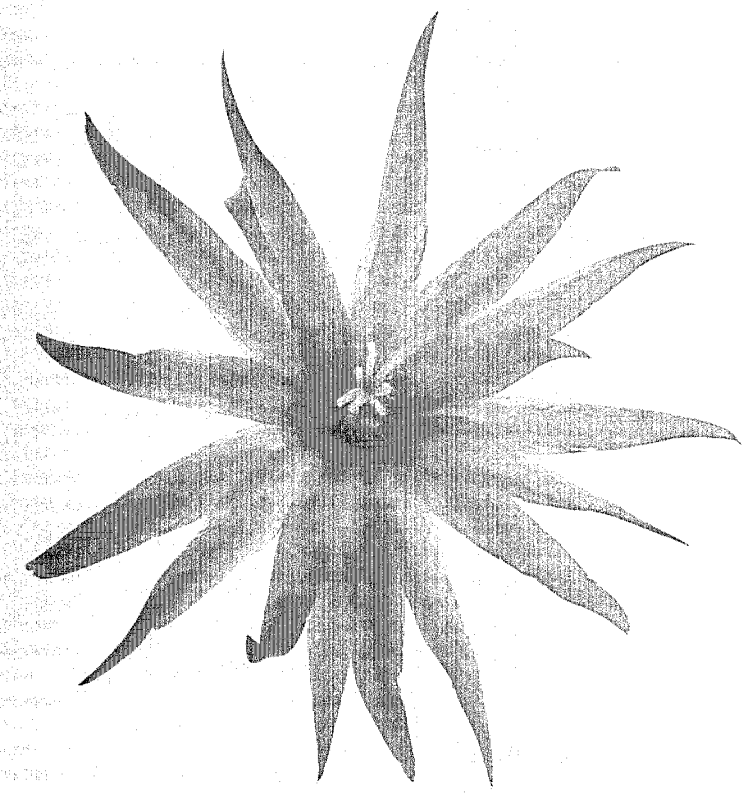
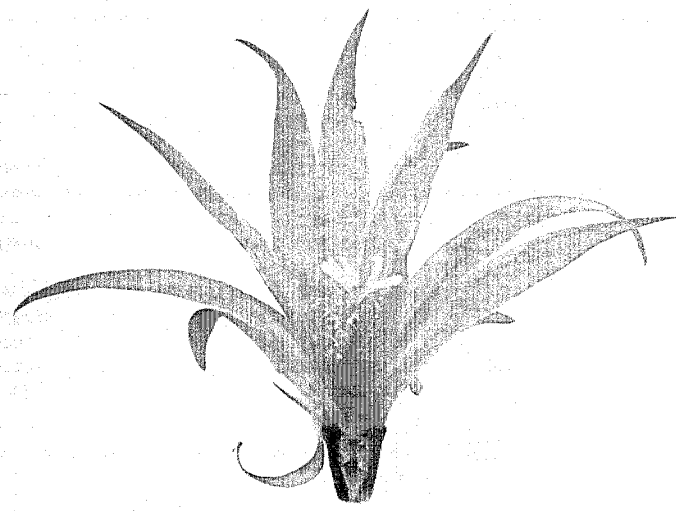

* * * * *